(12) United States Patent
Bierhoff et al.

(10) Patent No.: US 10,342,416 B2
(45) Date of Patent: Jul. 9, 2019

(54) MEDICAL PROBE WITH MULTI-FIBER LUMEN

(71) Applicant: KONINKLIJKE PHILIPS N.V., Eindhoven (NL)

(72) Inventors: Waltherus Cornelis Jozef Bierhoff, Veldhoven (NL); Axel Winkel, Zapel-Hof (DE); Bernardus Hendrikus Wilhelmus Hendriks, Eindhoven (NL); Stephan Voss, Schwerin (DE); Gerhardus Wilhelmus Lucassen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 163 days.

(21) Appl. No.: 14/348,623

(22) PCT Filed: Oct. 9, 2012

(86) PCT No.: PCT/IB2012/055449
§ 371 (c)(1),
(2) Date: Mar. 31, 2014

(87) PCT Pub. No.: WO2013/054254
PCT Pub. Date: Apr. 18, 2013

(65) Prior Publication Data
US 2014/0236024 A1 Aug. 21, 2014

Related U.S. Application Data

(60) Provisional application No. 61/546,696, filed on Oct. 13, 2011.

(51) Int. Cl.
*A61B 1/00* (2006.01)
*A61B 5/00* (2006.01)
(Continued)

(52) U.S. Cl.
CPC ........ *A61B 1/00167* (2013.01); *A61B 5/0071* (2013.01); *A61B 5/0084* (2013.01);
(Continued)

(58) Field of Classification Search
CPC ... A61B 1/00; A61B 10/0233; A61B 18/1477; A61B 1/00167; A61B 2562/223;
(Continued)

(56) References Cited

U.S. PATENT DOCUMENTS 4,200,096 A * 4/1980 Charvin ................ A61M 5/165
137/172
4,566,438 A 1/1986 Liese et al.
(Continued)

FOREIGN PATENT DOCUMENTS

CN 1794948 A 6/2006
CN 101904737 A 12/2010
(Continued)

OTHER PUBLICATIONS

T.J. Farrell et al., "A Diffusion Theory Model of Spatially Resolved, Steady-State Diffuse Reflectance for the Noninvasive Determination of Tissue Optical Properties in Vivo", Medical Physics, vol. 19, No. 4, Jul./Aug. 1992, pp. 879-888.
(Continued)

*Primary Examiner* — Amelie R Gillman

(57) ABSTRACT

The present invention relates to a medical probe which consists of a cannula with a multilumen stylet inside. The multilumen contains at least two lumen. Both the multilumen as well as the cannula may have beveled ends. In the lumen straight optical fibers (i.e. no angle end face) are present that can be connected at the proximal end to a console. The cannula, multilumen, fiber system forming the medical probe comprises at least in one of the lumen of the multilumen more than one optical fiber. Preferably the
(Continued)

source and detector fibers for the fluorescence detection are contained in one single lumen of the multilumen.

13 Claims, 6 Drawing Sheets

(51) Int. Cl.
*A61B 10/02* (2006.01)
*A61B 18/14* (2006.01)
(52) U.S. Cl.
CPC ........ *A61B 5/6848* (2013.01); *A61B 10/0233* (2013.01); *A61B 18/1477* (2013.01); *A61B 5/0075* (2013.01); *A61B 5/0086* (2013.01); *A61B 2562/223* (2013.01)
(58) Field of Classification Search
CPC ... A61B 5/0071; A61B 5/0075; A61B 5/0084; A61B 5/0086; A61B 5/6848
See application file for complete search history.

(56) References Cited

U.S. PATENT DOCUMENTS

| | | | | |
|---|---|---|---|---|
| 5,156,596 | A * | 10/1992 | Balbierz | A61M 25/0097 604/164.11 |
| 5,280,788 | A * | 1/1994 | Janes | A61B 5/0084 600/476 |
| 5,377,668 | A | 1/1995 | Ehmsen et al. | |
| 5,885,531 | A * | 3/1999 | Heffelfinger | G01N 21/64 422/50 |
| 6,564,088 | B1 | 5/2003 | Soller et al. | |
| 7,029,467 | B2 | 4/2006 | Currier et al. | |
| 7,945,312 | B2 | 5/2011 | Hular et al. | |
| 8,038,602 | B2 | 10/2011 | Gill et al. | |
| 8,123,745 | B2 | 2/2012 | Beeckler et al. | |
| 8,764,643 | B2 | 7/2014 | Fulghum | |
| 9,157,862 | B2 | 10/2015 | Zuluaga | |
| 2003/0045798 | A1 * | 3/2003 | Hular | A61B 5/0066 600/476 |
| 2003/0144594 | A1 | 7/2003 | Gellman | |
| 2004/0158136 | A1 * | 8/2004 | Gough | A61B 5/14546 600/328 |
| 2004/0254478 | A1 | 12/2004 | De Jong et al. | |
| 2005/0283048 | A1 | 12/2005 | Gill et al. | |
| 2006/0270900 | A1 * | 11/2006 | Chin | A61B 1/00096 600/104 |
| 2007/0038123 | A1 * | 2/2007 | Fulghum | A61B 5/0075 600/476 |
| 2007/0213588 | A1 | 9/2007 | Morishita et al. | |
| 2007/0265582 | A1 * | 11/2007 | Kaplan | A61B 17/3468 604/260 |
| 2008/0009751 | A1 * | 1/2008 | Berndt | A61B 5/0075 600/478 |
| 2009/0082695 | A1 * | 3/2009 | Whitehead | A61B 1/00052 600/562 |
| 2011/0071349 | A1 * | 3/2011 | Drontle | A61B 1/00165 600/106 |
| 2011/0098531 | A1 * | 4/2011 | To | A61B 1/32 600/114 |
| 2012/0226167 | A1 | 9/2012 | Zuluaga | |
| 2014/0236024 | A1 | 8/2014 | Waltherus et al. | |

FOREIGN PATENT DOCUMENTS

| | | | |
|---|---|---|---|
| EP | 0289021 | * | 4/1988 |
| JP | 2005501586 A | | 1/2005 |
| JP | 2006061457 A | | 3/2006 |
| WO | WO2010143119 | | 12/2010 |

OTHER PUBLICATIONS

R. Nachabe et al., "Estimation of Biological Chromophores Using Diffuse Optical Spectroscopy: Benefit of Extending The UV-VIS Wavelength Range to Include 1000 to 1600 nm", Optics Express, vol. 18, No. 24, Nov. 22, 2010, pp. 1432-1442.

R. Nachabe et al., "Estimation of Lipid and Water Concentrations in Scatter Media with Diffuse Optical Spectroscopy from 900 to 166 nm", Journal of Biomedical Optics 15(3), 1, May/Jun. 2010, pp. 1-1 through 1-10.

Q. Zhang et al., "Turbidity-Free Fluorescence Spectroscopy of Biological Tissue", Optics Letters, vol. 25, No. 19, Oct. 1, 2000, pp. 1451-1453.

* cited by examiner

MEDICAL PROBE WITH MULTI-FIBER LUMEN

CROSS-REFERENCE TO PRIOR APPLICATIONS

This application is the U.S. National Phase application under 35 U.S.C. § 371 of International Application Serial No. PCT/IB2012/055449, filed on Oct. 9, 2012, which claims the benefit of U.S. Application Ser. No. 61/546,696, filed on Oct. 13, 2011. These applications are hereby incorporated by reference herein.

FIELD OF THE INVENTION

The invention relates to a medical probe—such as biopsy needle, ablation needle or catheter—which incorporates optical fibers to perform optical measurements at the tip of the probe.

BACKGROUND OF THE INVENTION

In the field of oncology it is important to be able to discriminate tumor tissue from normal tissue. Typically, tissue is inspected at a pathology department after a biopsy or after surgical resection. A drawback of this current way of working is that real time feedback during the procedure of taking a biopsy or performing the surgical resection is missing. A way to provide such feedback to a medical device or medical probe, for instance a biopsy needle, is to incorporate optical fibers to perform optical measurements at the tip of the medical probe.

Various optical methods can be employed with diffuse reflectance (DRS) and autofluorescence measurement as the techniques that are most commonly investigated. Several probes can be used to perform these measurements but in general these probes have blunt end surfaces and are therefore difficult to combine as a direct integral part of a single medical probe.

The U.S. Pat. No. 4,566,438 discloses a sharp fiber-optic stylet in which two optical fibers are incorporated that could perform DRS and fluorescence measurements at the tip of the needle. However the optical fibers in the stylet are beveled and as a result a significant part of the light in the optical fiber will undergo total internal reflection at the tip of the needle, reaching the cladding material of the optical fiber and then exiting the optical fiber. This travelling through the buffer can cause a significant amount of unwanted autofluorescence of the cladding material hampering the measurement of the tissue autofluorescence.

SUMMARY OF THE INVENTION

It is an object of the invention to provide a medical probe system with increased optical detection efficiency.

This object is achieved by a medical probe as claimed in claim 1 and by an optical measurement system as claimed in claim 9.

Accordingly, the multilumen insert (e.g. multilumen tube, multilumen stylet etc.) has at least one multi-fiber lumen that can contain more than one fiber. Hence there is no side wall between these two fibers and no shadowing effect can occur. The fibers used in the multi-fiber lumen are straight cut or only a moderate angle in such a way that (partly) total internal reflection at the fiber end is prevented. The location and orientation of a fiber are fixed with regard to the multilumen insert and thus also with regard to other fibers of the multilumen insert. The medical probe may be a biopsy needle, an ablation needle or another type of needle or catheter which can be used as a medical probe.

According to a first aspect, the at least two optical fibers comprise source and detector fibers for fluorescence detection. This provides the advantage that fluorescence collection efficiency at the tip of the probe can be improved due to the missing side wall.

According to a second aspect which may be combined with the first aspect, the at least two optical fibers are placed against each other to have the smallest fiber core distance and therefore increase collection efficiency.

According to a third aspect which can be combined with any one of the first and second aspects, the multi-fiber lumen of the multilumen insert comprises three optical fibers. Thereby, an additional fiber can be used for conveying light to or from the tip of the needle.

According to a fourth aspect which can be combined with any one of the first to third aspects, the multilumen insert is beveled by an angle that is smaller than the angle of bevel of the cannula. Thereby, when assembling the fiber inside the multilumen insert they may protrude somewhat without protruding beyond the level of the cannula.

According to a fifth aspect which can be combined with any one of the first to fourth aspects, the multi-fiber lumen may be partly or completely coated with a metal coating or a coating having low autofluorescence. Thereby, unwanted autofluorescence from other needle parts can be reduced.

According to a sixth aspect which can be combined with any one of the first to fifth aspects, the detector of the optical measurement system is adapted to detect tissue-generated fluorescence at increased efficiency through the at least one other of the at least two optical fibers.

According to a seventh aspect which can be combined with any one of the first to sixth aspects, at least one of the light source and the detector provides wavelength selectivity. This measure enables diffuse reflectance measurements.

According to an eighth aspect which can be combined with any one of the first to seventh aspects, the detector is adapted to filter out excitation light using a detection filter. Thereby, possible overload of the detector by excitation light can be prevented.

According to a ninth aspect which can be combined with any one of the first to eighth aspects, the optical measurement system is adapted to combine fluorescence measurements with diffuse reflectance measurements by providing at least one of a fiber switch, a beam splitter and a dichroic beam combiner with focusing optics, and wherein the one of the at least two optical fibers conveys excitation light for measuring fluorescence and light for diffuse reflectance.

According to a tenth aspect which can be combined with any one of the first to ninth aspects, the system is adapted to derive optical tissue properties which are different between normal healthy tissue and diseased tissue. Thereby, the system is able to discriminate different tissue types, e.g., tumor tissue from normal tissue.

Further advantageous embodiments are defined below.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

Various embodiments are now described based on an optical measurement system comprising an optical console and a biopsy needle (as one example of a medical probe to which the present invention can be applied) for discriminating tumor tissue from normal tissue. It is however noted that the present invention can also be applied to another medical probe which can be, for instance, any slender, flexible surgical instrument with a tip, used to explore a wound, body cavity or body tissue.

In order to provide an effective medical probe with optical fibers incorporated therein, a number of requirements are preferentially fulfilled: The probe should be sharp or thin.

Integrating the optical fibers into the probe should not alter the penetration properties into the tissue.

The distance between the excitation fiber end for fluorescence and the fluorescence detection fiber should be small.

The autofluorescence of the probe should be small compared to that generated in the tissue.

The shading effects of the multilumen tube should be small.

The autofluorescence by the optical fiber itself should be small compared to the measured tissue signal.

The optical fibers in the probe may not extend beyond the bevel of the cannula.

The probe should be compatible with mass production.

The cost of the probe should be sufficiently low in order to make it disposable (because of the difficulty of sterilizing used probes they are in general disposable).

For correcting fluorescence signals for absorption and scattering, a DRS measurement should be done with more than one optical fiber.

Because of all these constraints it is far from trivial to find a solution that fulfils all these requirements.

Figure 1:
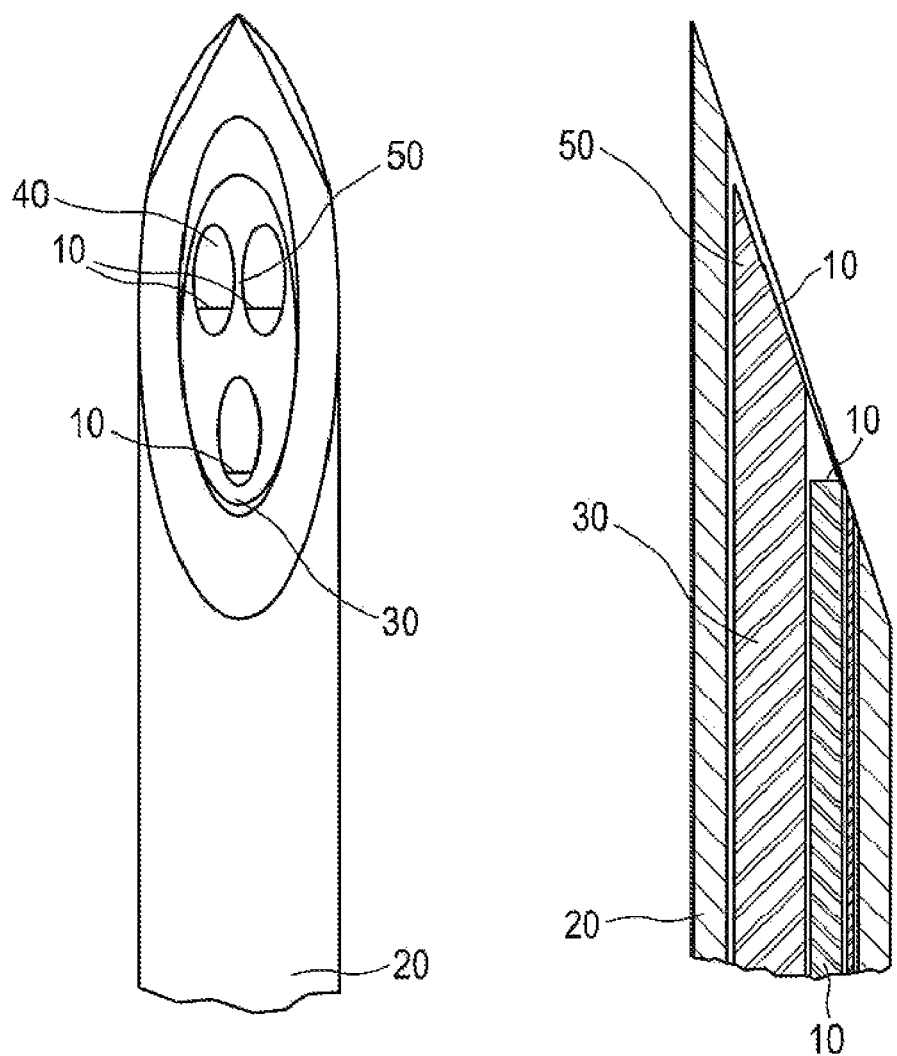
FIG. 1 shows a schematic front, top and sectional side view of an exemplary biopsy needle with integrated optical fibers that is hampered by low fluorescence detection efficiency.
Figure 1:
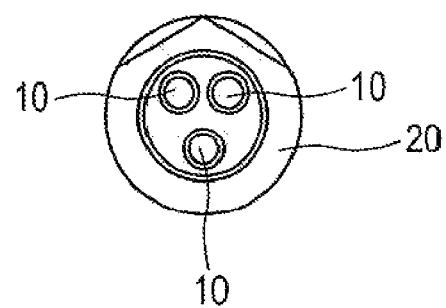

FIG. 1 shows a schematic front, top and sectional side view of an example of a design of a biopsy needle that might be a good option. A surrounding cannula 20 with beveled end includes a multilumen tube 30 having three lumen 40 through which respective optical fibers 10 are guided. Due to the beveled end of the multilumen tube 30, pockets are formed at the ends of the lumen 40. End faces of the straight-cut optical fibers 10 can be seen in the pockets of the lumen 40. Furthermore, pocket side walls 50 are formed between the upper two lumen 40. However, the exemplary biopsy needle of FIG. 1 with integrated optical fibers is hampered by low fluorescence detection efficiency. Therefore, this design has poor performance regarding the above point 5, for example. More specifically, the side wall 50 between the two adjacent optical fibers at the top position is significantly hampering the fluorescence collection efficiency.

The following embodiments are related to a biopsy needle as one example of the medical probe to which the present invention can be applied in general.

Figure 2:
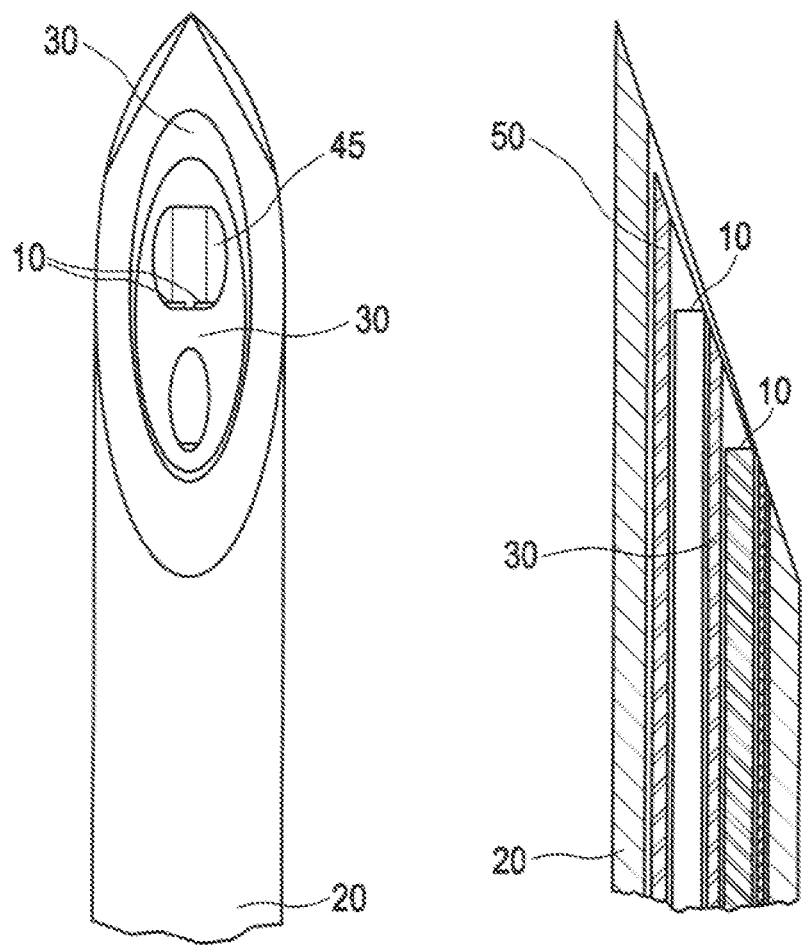
FIG. 2 shows a schematic front, top and sectional side view of an exemplary biopsy needle with integrated optical fibers according to a first embodiment.
Figure 2:
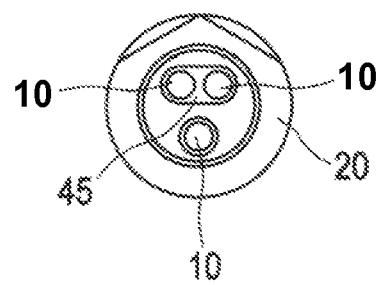
Figure 3:
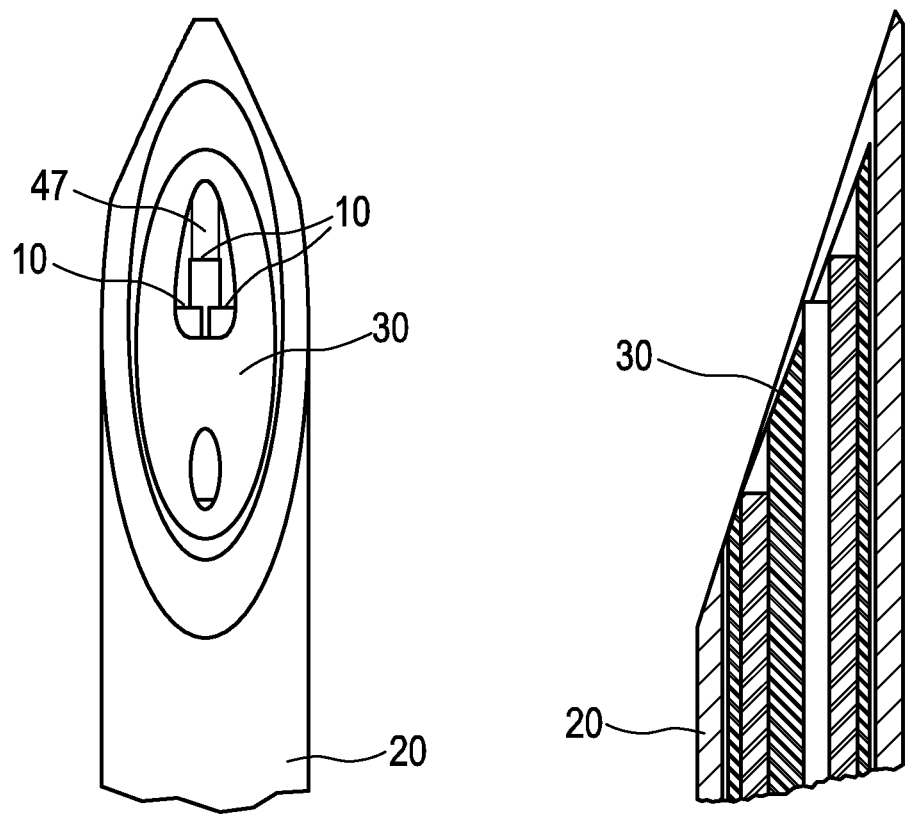
FIG. 3 shows a schematic front, top and sectional side view of an exemplary biopsy needle with integrated optical fibers according to a second embodiment.
Figure 3:
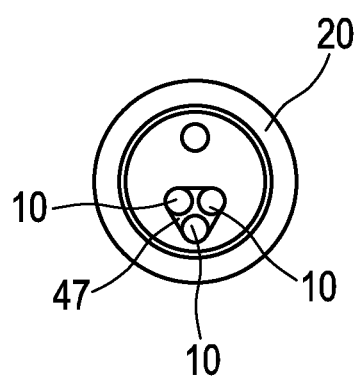
Figure 4A:
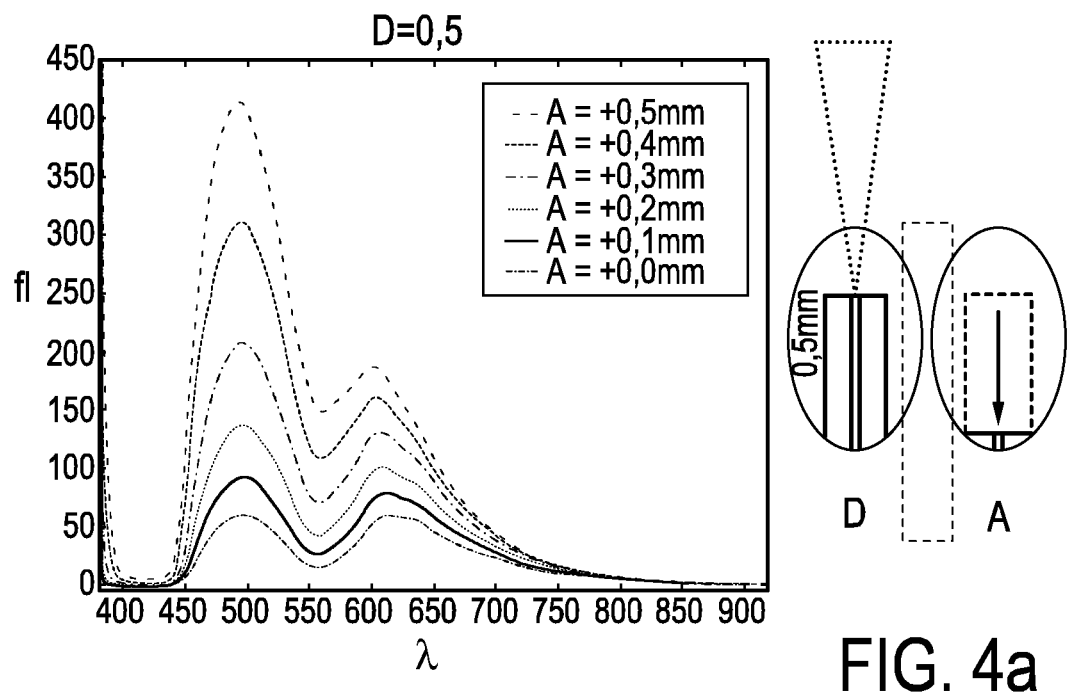
FIG. 4 shows various plots of measured fluorescence of optical fibers separated by a side wall based on the amount of their protrusion beyond the pocket of their lumen.
Figure 4B:
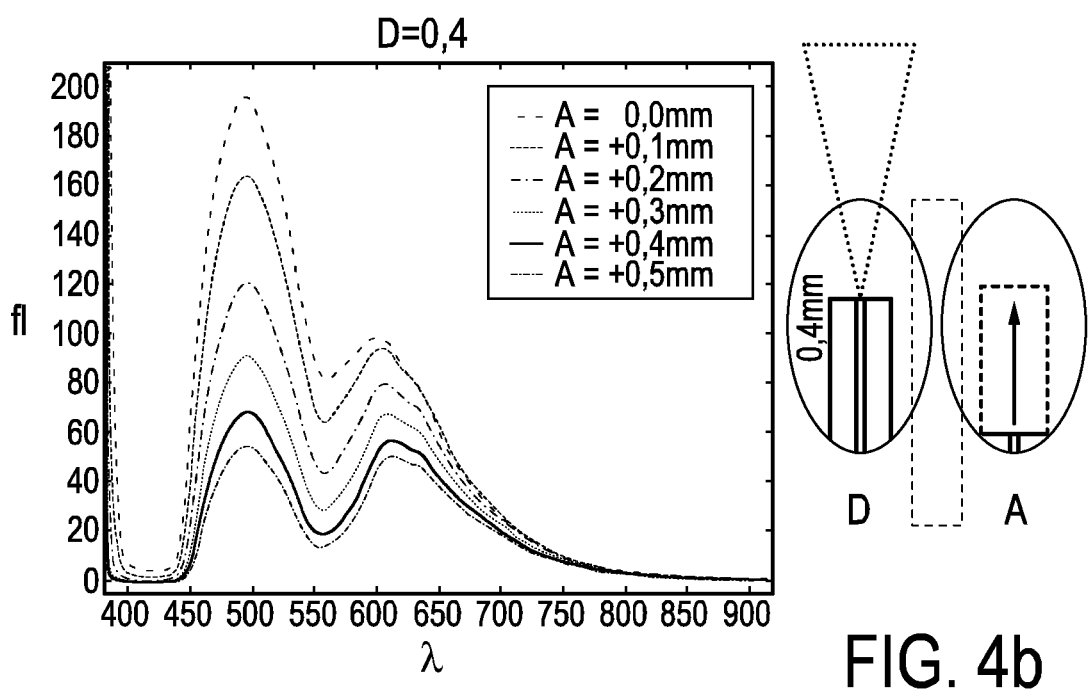
Figure 4C:
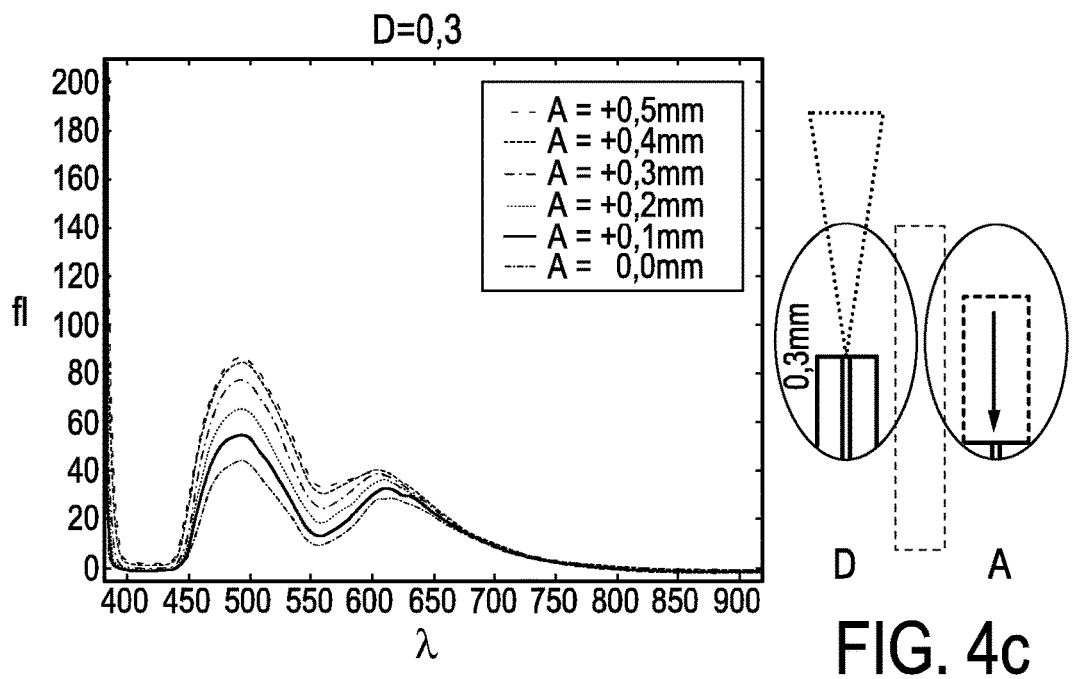
Figure 4D:
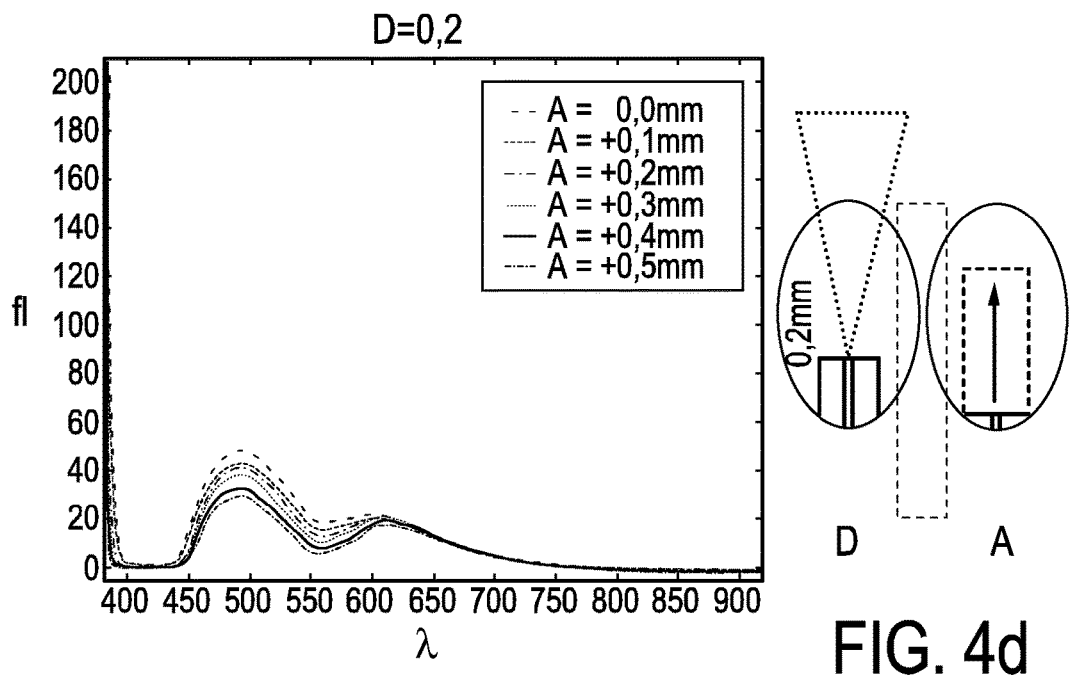
Figure 4E:
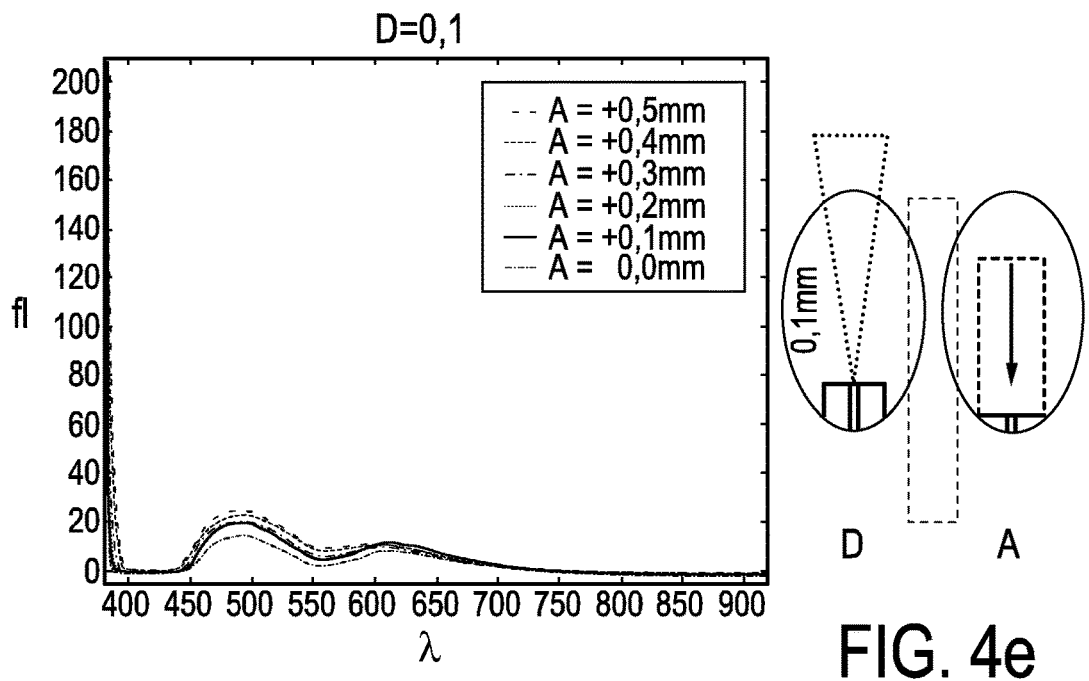
Figure 4F:
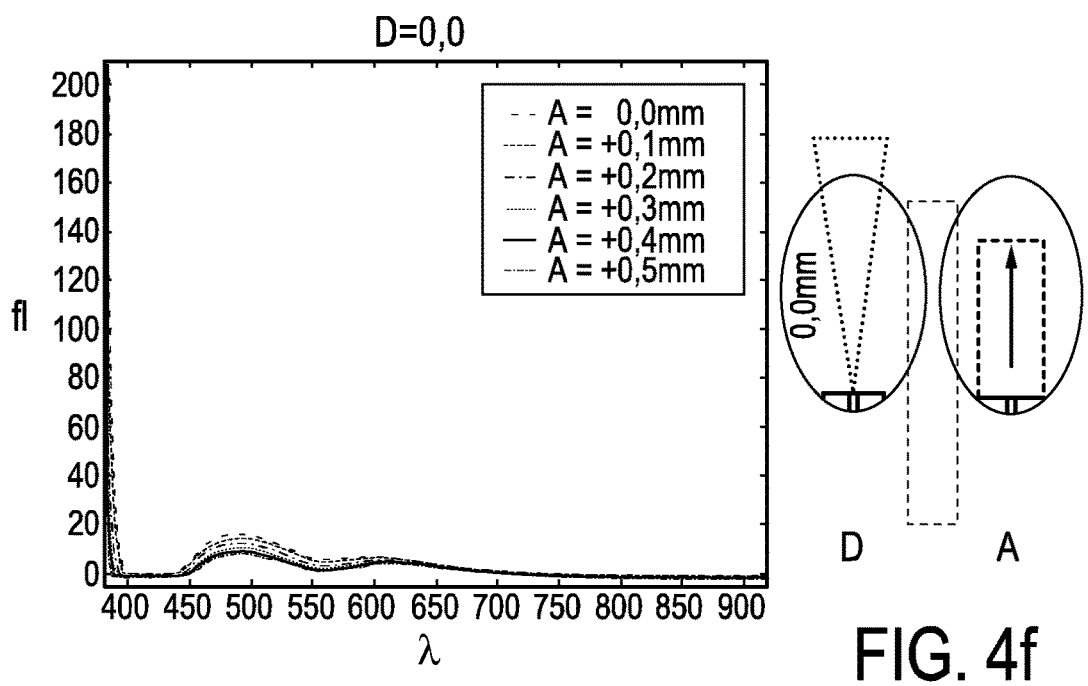

FIGS. 2 and 3 show schematic front, top and sectional side views of biopsy needles according to first and second embodiments. These biopsy needles provide enhanced collection efficiency and each comprise a cannula 20 with a multilumen tube 30 inside. The multilumen tube 30 contains two lumen and the multilumen tube 30 as well as the cannula 20 both have beveled ends. In the lumen substantially straight cleaved fibers 10 (i.e. angle end face is small such that no total internal reflection at the interface can take place) are provided which can be connected at their proximal end to an optical console. Similar to FIG. 1, the cannula 20, the multilumen tube 30, and the fiber system form the biopsy needle. However, according to the first and second embodiments, a multi-fiber lumen 45, 47 which contains more than one fiber 10 is provided in the multilumen tube 30. The shape and size of the multi-fiber lumen 45, 47 are adapted to the enclosed or incorporated optical fibers 10 so that the orientation of the enclosed or incorporated optical fibers 10 is mutually fixed and the fibers are aligned.

In the first embodiment shown in FIG. 2, source and detector fibers for the fluorescence detection are contained in one multi-fiber lumen 45 of the multilumen tube 30. Furthermore, in the specific example of the first embodiment of FIG. 2, these fibers in the multi-fiber lumen 45 are placed against each other to have the smallest fiber core distance between these fibers.

In the second embodiment shown in FIG. 3, a multi-fiber lumen 47 which contains three optical fibers 10 is provided. Thereby, a further optical fiber is available for improving the detection efficiency.

Thus, as can be gathered from FIGS. 2 and 3, the multilumen insert 30 is formed in a manner to provide a fixed distance and orientation of the contained optical fibers 10. The shape of the multi-fiber lumen 45, 47 is adapted to the number of optical fibers 10 contained therein, so that the location and orientation of the optical fibers 10 are fixed with regard to the multilumen insert 30 and thus also to any other optical fiber 10 in the multilumen insert 30.

In a third embodiment (not shown), the multi-fiber lumen 45 or 47 of the first or second embodiment may be partly or completely coated with a metal coating or a coating having low autofluorescence such that unwanted autofluorescence from needle parts (such as the multilumen tube 30) are as low as possible.

To manufacture the biopsy needle, the multilumen tube 30 may be made of plastic material with well defined lumen at positions that define the distance between the optical fibers 10 that can be inserted in these lumen. In the first to third embodiment, the multilumen tube 30 has at least one multi-fiber lumen 45, 47 that can contain more than one optical fiber 10. Hence there is no side wall between these two or three optical fibers 10 and no shadowing effect can occur. These two or three optical fibers 10 in the multi-fiber lumen 45, 47 are therefore well suited for fluorescence detection.

The optical fibers 10 used in the multi-fiber lumen 45, 47 are typically straight cut or only a moderate angle in such a way that (partly) total internal reflection at the fiber end is prevented. When total internal reflection occurs light reflected at the fiber end will end up in the cladding of the optical fiber 10. Depending on what material surrounds the optical fiber 10, part of this light will be reflected back into the core of the optical fiber 10 and is able to leave the optical fiber 10. For diffuse reflectance this is less of a problem but for fluorescence it causes a significant amount of background fluorescence. This hampers investigation of the fluorescence generated by the tissue.

As an option, the multilumen tube 30 may be beveled at the distal end by an angle that is smaller than the angle of the bevel of cannula 20. In this way when assembling the optical fibers 10 inside the multilumen tube 30 they may protrude somewhat without protruding beyond the bevel of the cannula 20. This provides the advantage that insertion properties of the needle in the tissue are not affected.

A simple way to assemble the optical fibers 10 in the multilumen tube 30 is by positioning the fiber end equal to the start or edge of the pocket (see FIG. 2). Other ways of assembling are also envisioned without departing the scope of the invention. The reasoning behind this solution can be inferred from the following.

FIG. 4 shows various plots of measured fluorescence of optical fibers separated by a side wall (as shown in FIG. 1) based on the amount of their protrusion beyond the lower end of the pocket of their lumen. In each of the plots, a first optical fiber D is kept at a predetermined distance from the lower edge of the pocket, while the other optical fiber A is moved from a distance 0.0 mm to 0.5 mm. The less the fibers protrude beyond the start or lower end of the pocket the smaller the signal. Clearly the side wall of the pockets of the fibers A and D are blocking part of the signal. Consider the measurements shown in FIG. 4, when the fibers are substantially equal to the start of the pocket the shading effect of the walls of the pockets is significant leading to smaller signals. So in this case although the distance between the fiber does not change when they both protrude the same amount beyond the start of the pocket, the signal becomes higher when they protrude more because of the reduced effect of the side wall of the pocket. Therefore, in case of fluorescence imaging the presence of the side wall between the source and detection fiber is unwanted. Therefore, in the above embodiments, the sidewall between the two fibers has been removed by placing them in a single multi-fiber lumen.

The multilumen tube 30 can be produced in mass production. Producing straight cut fibers is straightforward and can be done in batches. Assembling fibers in the multilumen tube 30 can be well controlled making these needles compatible with mass production. Furthermore, because of this way of assembling, a rather low cost needle can be assured.

The biopsy needle according to the above embodiments can be connected to an optical console. The optical console contains a light source enabling light to be provided via one or more of the fibers to the distal end of the optical probe. The scattered light is collected by one or more other fibers and is guided towards the detector or detectors. The amount of reflected light measured at the "detection" fiber, is determined by the absorption and scattering properties of the probed structure (e.g. tissue). The data are processed using a dedicated algorithm. For diffuse reflectance measurements, either the light source or the detector or a combination of both may provide wavelength selectivity. For instance, light can be coupled out of the distal tip through at least one fiber, which serves as a source, and the wavelength is swept from e.g. 500-1600 nm, while the light detected by at least one detection fiber is sent to a broadband detector. Alternatively, broadband light can be provided by at least one source fiber, while the light detected by at least one detection fiber is sent to a wavelength-selective detector, e.g. a spectrometer.

For a detailed discussion on diffuse reflectance measurements see for example R. Nachabé, B. H. W. Hendriks, A. E. Desjardins, M. van der Voort, M. B. van der Mark, and H. J. C. M. Sterenborg, "Estimation of lipid and water concentrations in scattering media with diffuse optical spectroscopy from 900 to 1600 nm", J. Biomed. Opt. 15, 037015 (2010).

For fluorescence measurements the console may be capable of providing excitation light to at least one source fiber while detecting tissue-generated fluorescence through one or more detection fibers. The excitation light source can be a laser (e.g. a semiconductor laser), a light-emitting diode (LED) or a filtered light source, such as a filtered mercury lamp. In general, the wavelengths emitted by the excitation light source are shorter than the range of wavelengths of the fluorescence that is to be detected. The excitation light may be filtered out using a detection filter in order to avoid possible overload of the detector by the excitation light. A wavelength-selective detector, e.g. a spectrometer, may be used when multiple fluorescent entities are present that need to be distinguished from each other.

In case fluorescence measurements are to be combined with diffuse reflectance measurements, the excitation light for measuring fluorescence can be provided to the same source fiber as the light for diffuse reflectance. This can be accomplished by, e.g., using a fiber switch, or a beam splitter or dichroic beam combiner with focusing optics. Alternatively, separate fibers can be used for providing fluorescence excitation light and light for diffuse reflectance measurements.

Although diffuse reflectance spectroscopy has been described above to extract tissue properties, also other optical methods can be envisioned like diffuse optical tomography by employing a plurality of optical fibers, differential path length spectroscopy, Raman spectroscopy. Furthermore, the proposed optical measurement system may also be employed when contrast agents are used instead of only looking at autofluorescence.

In the optical measurement system using the biopsy needle according to the above embodiments, an algorithm may be used to derive optical tissue properties such as the scattering coefficient and absorption coefficient of different tissue chromophores: e.g. hemoglobin, oxygenated haemoglobin, water, fat etc. These properties are different between normal healthy tissue and diseased (cancerous) tissue.

In more detail the algorithm can be described as follows. The spectral fitting can be performed by making use of the analytically derived formula for reflectance spectroscopy, as described for example in T. J. Farrel, M. S. Patterson and B. C. Wilson, "A diffusion theory model of spatially resolved, steady-state diffuse reflectance for the non-invasive determination of tissue optical properties," Med. Phys. 19 (1992) p 879-888 or R. Nachabé, B. H. W. Hendriks, A. E. Desjardins, M. van der Voort, M. B. van der Mark, and H. J. C. M. Sterenborg, "Estimation of lipid and water concentrations in scattering media with diffuse optical spectroscopy from 900 to 1600 nm", J. Biomed. Opt. 15, 037015 (2010). The reflectance distribution R is given by $$R(\rho) = \int_0^\infty R(\rho, z_0) \delta(z_0 - 1/\mu_t') dz_0 \qquad (1)$$

$$= \frac{a'}{4\pi} \left[ \frac{1}{\mu_t'} \left( \mu_{eff} + \frac{1}{\tilde{r}_1} \right) \frac{e^{-\mu_{eff} \tilde{r}_1}}{\tilde{r}_1^2} + \left( \frac{1}{\mu_t'} + 2z_b \right) \left( \mu_{eff} + \frac{1}{\tilde{r}_2} \right) \frac{e^{-\mu_{eff} \tilde{r}_2}}{\tilde{r}_2^2} \right]$$

where $$\tilde{r}_1 = [x^2 + y^2 + (1/\mu_t')^2]^{1/2}$$

$$\tilde{r}_2 = [x^2 + y^2 + ((1/\mu_t') + 2z_b)^2]^{1/2}$$

$$\mu_{\mathit{eff}} = \sqrt{3\mu_a[\mu_a + \mu_s(1-g)]}$$

In this formula the three macroscopic parameters describing the probability of interaction with tissue are: the absorption coefficient $\mu_a$ and the scattering coefficient $\mu_s$ both in $cm^{-1}$ as well as by g which is the mean cosine of the scattering angle. Furthermore, we have the total reduced attenuation coefficient $\mu_t'$ that gives the total chance for interaction with tissue $$\mu_t' = \mu_a + \mu_s(1-g). \tag{2}$$

The albedo a' is the probability of scattering relative to the total probability of interaction $$a' = \mu_s/\mu_t'. \tag{3}$$

It is assumed that a point source at a depth $z_0=1/\mu_t'$ and no boundary mismatch hence $z_b=2/(3\mu_t')$. Furthermore, it is assumed that the scattering coefficient can be written as $$\mu_s'(\lambda) = \alpha\lambda^{-b}. \tag{4}$$

The main absorbing constituents in normal tissue dominating the absorption in the visible and near-infrared range are blood (i.e. hemoglobin), water and fat. It is noted that blood dominates the absorption in the visible range, while water and fat dominate in the near infrared range.

The total absorption coefficient is a linear combination of the absorption coefficients of for instance blood, water and fat. By fitting the above formula while using the power law for scattering, the volume fractions of the blood, water and fat as well as the scattering coefficient can be determined. With this method the measured spectra can be translated in physiological parameters that can be used to discriminate different tissues.

Another way to discriminate differences in spectra is by making use of a principal components analysis. This method allows classification of differences in spectra and thus allows discrimination between tissues. It is also possible to extract features from the spectra.

The measured fluorescence may be affected by the absorption and scattering of light in the tissue that may hamper the tissue analysis. In some cases it can be better to correct the measured fluorescence for these scattering and absorption effects. How to extract the intrinsic fluorescence from the measured fluorescence can be found for instance in Zhang et al., Optics Letters 25 (2000) p 1451 and is here included by reference.

To summarize, a medical probe has been described based on an exemplary biopsy needle, which consists of a cannula with a multilumen stylet inside. The multilumen contains at least two lumen. Both the multilumen as well as the cannula have beveled ends. In the lumen straight optical fibers (i.e. no angle end face) are present that can be connected at the proximal end to a console. The cannula, multilumen, fiber system forming the medical probe comprises at least in one of the lumen of the multilumen more than one optical fiber. Preferably the source and detector fibers for the fluorescence detection are contained in one single lumen of the multilumen.

While the invention has been illustrated and described in detail in the drawings and foregoing description, such illustration and description are to be considered illustrative or exemplary and not restrictive; the invention is not limited to the disclosed embodiments and can be used for various types of medical probes where optical fibers are placed in lumen or multilumen. Furthermore, it is noted that the term "medical probe" as used in the context of the present application can be interpreted in a manner to include, for example, interventional devices like needles, in particular, ablation needles (such as used for radio frequency ablation) or more flexible catheter-like devices. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A medical probe comprising:
   a cannula (20) having a multilumen insert (30), and
   at least two optical fibers (10) each having a longitudinal axis and an end face, the at least two optical fibers being arranged in a multi-fiber lumen (45; 47) of said multilumen insert (30);
   wherein the shape and size of said multi-fiber lumen (45; 47) is adapted to said at least two optical fibers (10) so that the orientation of said at least two optical fibers (10) is mutually fixed by the multi-fiber lumen,
   wherein the end face of each of the at least two optical fibers is square to the longitudinal axis of the respective optical fiber;
   wherein said cannula (20) and said multilumen insert (30) have beveled ends surrounding said multi-fiber lumen and wherein the at least two optical fibers (10) do not extend beyond the bevel of the cannula (20).

2. The probe according to claim 1, wherein said at least two optical fibers (10) comprise source and detector fibers for fluorescence detection.

3. The probe according to claim 1, wherein said at least two optical fibers (10) are placed against each other.

4. The probe according to claim 1, wherein said at least two optical fibers (10) comprises three optical fibers (10).

5. The probe according to claim 1, wherein said multilumen insert (30) is beveled by an angle that is smaller than the angle of bevel of said cannula (20).

6. The probe according to claim 1, wherein said multi-fiber lumen (45; 47) is at least partly coated with a metal coating.

7. The probe according to claim 1, wherein said probe comprises a biopsy needle, an ablation needle, or a catheter.

8. An optical measurement system comprising a medical probe and an optical console to which said medical probe is connectable,
   wherein the medical probe comprises a cannula having a multilumen insert and at least two optical fibers (10) each having a longitudinal axis and an end face, the at least two optical fibers being arranged in a multi-fiber lumen (45; 47) of said multilumen insert (30),
   the shape and size of said multi-fiber lumen (45; 47) is adapted to said at least two optical fibers (10) so that the orientation of said at least two optical fibers (10) is mutually fixed by the multi-fiber lumen,
   the end face of each of the at least two optical fibers is square to the longitudinal axis of the respective optical fiber, said cannula (20) and said multilumen insert (30) have beveled ends surrounding said multi-fiber lumen, and the at least two optical fibers (10) do not extend beyond the bevel of the cannula (20); and wherein said optical console comprises a light source and a detector, the light, source providing light to a distal end of said medical probe via one of said at least two optical fibers (10), wherein scattered light is guided by at least one other of said at least two optical fibers (10) towards the detector.

9. The system according to claim 8, wherein said detector is adapted to detect tissue-generated fluorescence through said at least one of said at least two optical fibers (10).

10. The system according to claim 8, wherein at least one of said light source and said detector provides wavelength selectivity.

11. The system according to claim 8, wherein said detector is adapted to filter out excitation light using a detection filter.

12. The system according to claim 8, wherein said system comprises at least one of a fiber switch, a beam splitter and a dichroic beam combiner with focusing optics, to combine fluorescence measurements with diffuse reflectance measurements, and wherein said one of said at least two optical fibers (10) conveys excitation light for measuring fluorescence and light for diffuse reflectance.

13. The system according to claim 8, further comprising a processor adapted to derive optical tissue properties to discriminate different tissue types.

* * * * *